(12) United States Patent
Anne et al.

(10) Patent No.: US 6,503,726 B2
(45) Date of Patent: Jan. 7, 2003

(54) CHROMOGENIC SUBSTRATE TO DETECT URINE ADULTERATION

(75) Inventors: Lakshmi Anne, Hayward, CA (US); Weixing Luo, Sunnyvale, CA (US); Ker-kong Tung, Del Mar, CA (US)

(73) Assignee: Applied Biotech, Inc., San Diego, CA (US)

( * ) Notice: Subject to any disclaimer, the term of this patent is extended or adjusted under 35 U.S.C. 154(b) by 85 days.

(21) Appl. No.: 09/794,789

(22) Filed: Feb. 27, 2001

(65) Prior Publication Data

US 2002/0160439 A1 Oct. 31, 2002

(51) Int. Cl.[7] ............ C12Q 1/28; C12Q 1/00; G01N 33/53
(52) U.S. Cl. ............ 435/28; 435/4; 435/283.1; 435/970; 436/111
(58) Field of Search .......... 435/28, 4, 283.1, 435/970; 436/111

(56) References Cited

U.S. PATENT DOCUMENTS 6,303,384 B1 * 10/2001 Mills et al. .............. 436/111

FOREIGN PATENT DOCUMENTS

WO 2001754444 * 10/2001

OTHER PUBLICATIONS

Boehringer, Mannheim Corporation (Indianapolis, IN), *Cedia Dau Sample Check*, Oct. 1997, Package Insert.
Singh et al., *The Measurement of Nitrite in Adulterated Urine Samples by High–Performance Ion Chromatography*, 1999, Journal of Analytical Toxicology, 23, pp. 137–140.
*Stealth Catalytic Purifier*, Package Insert, (Date Unknown, initially purchased May 1998), www.Timesoft.com.
Wu et al., *Adulteration of Urine by "Urine Luck"*, 1999, Clinical Chemistry, 45, pp. 1051–1057.
Cannabis Connections, *Drug Test Kits*, Mar. 14, 2000, www.Timesoft.com.
Diagnostic Reagents, Inc. (Sunnyvale, CA), *Chromate–Detect Test*, Jul. 1999, Package Insert.
Diagnostic Reagents, Inc. (Sunnyvale, CA), *Creatinine–Detect Test*, Nov. 1999, Package Insert.
Diagnostic Reagents, Inc. (Sunnyvale, CA), *Gravity–Detect Test*, Aug. 1999, Package Insert.
Diagnostic Reagents, Inc. (Sunnyvale, CA), *Nitrite–Detect Test*, Jul. 1999, Package Insert.
Harlow and Lane, *Antibodies: A Laboratory Manual*, 1988, Cold Spring Harbor Laboratory, New York, pp. 680–681.
King, *Performance of AdultCheck 4 Test Strips for the Detection of Adulteration at the Point of Collection of Urine Specimens Used for Drugs–of–Abuse Testing*, 1999, Journal of Analytical Toxicology, 23, p. 72.
Lewis et al., *Potassium Nitrite Reaction with 11–Nor–Delta9–Tetrahydrocannabinol–9–Carboxylic Acid in Urine in Relation to the Drug Screening Analysis*, 1999, Journal of Forensic Sciences, 44, pp. 951–955.

* cited by examiner

Primary Examiner—Louise N. Leary
(74) Attorney, Agent, or Firm—Wood, Herron & Evans, L.L.P.

(57) ABSTRACT

A device and method to detect oxidant adulterants added to a sample to prevent detection of tetrahydrocannabinol and/or tetrahydrocannabinol metabolites. The device and method detect popularly available adulterants such as chromate and nitrite through their reaction with a chromogenic substrate for a peroxidase enzyme. The substrate may be applied to a pad. A change in color in the presence of the oxidant may be detected directly or indirectly. The device and method may be used to detect the presence of any oxidant adulterant and is not specific for only one or a few adulterants added to a urine sample submitted for drug testing.

17 Claims, No Drawings

CHROMOGENIC SUBSTRATE TO DETECT URINE ADULTERATION

FIELD OF THE INVENTION

The invention is directed generally to a composition and method that detects whether a urine sample submitted for drug testing contains an oxidant chemical adulterant.

BACKGROUND

Individuals may be requested or required to provide a urine sample that will be tested for the presence of drugs of abuse or metabolites of drugs of abuse. An initial or screening test is frequently performed first. A positive result is usually confirmed by a method different from that used for initial testing and usually having greater sensitivity and specificity. An initial negative test, however, is usually not confirmed. Thus, an individual who is fearful of a positive result in an initial screening test may alter his or her urine sample to prevent detection of the drug or drug metabolite.

One method of altering a urine sample is by diluting the sample so that the drug or drug metabolite concentration is below the detection threshold in a screening test. For example, water and/or saline may be added to the sample to dilute the drug or its metabolite to a concentration that is less readily detected by the screening test. To detect this type of alteration, the urine sample is frequently assayed to determine if physiological parameters such as creatinine concentration, pH, and specific gravity are within normal ranges, or if these parameters are abnormal due to the presence of diluent.

Chemical adulterants may be added to the sample to chemically convert a drug metabolite to a less detectable or non detectable product. Such chemicals include nitrite and chromate. The presence of chemical adulterants is more difficult to assess, since tests for the specific chemicals must be performed. For example, a group of adulterants has recently been developed to chemically modify 11-nor-delta-9-tetrahydrocannabinol-9-carboxylic acid ($\Delta^9$THC), a metabolite of marijuana. These adulterants prevent recognition of $\Delta^9$THC by drug screening and/or confirmatory assays, but do not otherwise affect the assays. These adulterants do not alter physical and/or chemical properties of the sample, such as pH and specific gravity, which are commonly monitored to detect urine adulteration.

As each new chemical adulterant is recognized and identified, tests are developed for identification of the specific adulterant. However, with the development of multiple adulterants, each of which is chemically distinct and each of which is capable of destroying or masking THC metabolites, the process of identifying adulterated urine samples becomes increasingly difficult. Multiple tests must be performed on each sample to assure detection of all chemically adulterated samples. Furthermore, there is a period of time for each adulterant during which samples containing that adulterant are not detected because the test-specific adulterant has not yet been identified and/or confirmed.

Thus, there is a need for a composition and method that detect a group of adulterants that are added to urine to prevent detection of marijuana use.

SUMMARY OF THE INVENTION

The invention is directed to compounds and methods that detect a group of adulterants in urine which are designed to oxidize, and thus prevent detection of 11-nor-delta-9-tetrahydrocannabinol-9-carboxylic acid ($\Delta^9$THC).

The invention is also directed to a device to detect adulteration of a biological sample with a chemical oxidant that prevents detection of marijuana use. The sample is contacted with a pad containing a substrate for an enzyme that forms a colored product in the presence of the oxidant. The pad may be affixed to a backing to form a test strip, and may have a sample application site. The chromogenic substrate on the pad may be 3,3',5,5'-tetramethylbenzidine, diaminobenzidine, 3-amino-9-ethylcarbazone, 4-chloro-1-napthol, 2,2-azino-bis(3-ethylbenzthiazoline-6-sulfonic acid, and ortho-phenylenediamine.

The invention is also directed to a method to detect an oxidant adulterant added by an individual to a urine sample to prevent detection of marijuana use by the individual. In the method, a sample is reacted with a chromogenic substrate for a peroxidase, then is monitored for production of a chromogen, which indicates that an oxidant adulterant was present in the sample. The oxidant chemical may be nitrite, such as potassium nitrite or sodium nitrite, or chromium VI such as pyridinium chlorochromate, or peroxidase and hydrogen peroxide ($H_2O_2$). The sample may be monitored on a test strip containing the chromogenic substrate, or by a clinical analyzer set at a wavelength to monitor production of the chromogen.

The invention will be further appreciated with reference to the following detailed description and examples.

DETAILED DESCRIPTION

The inventive compositions and methods detect members of the group of adulterants that chemically modify 11-nor-delta-9-tetrahydrocannabinol-9-carboxylic acid ($\Delta^9$THC). Individuals adulterating urine samples with these chemicals likely appreciate that oxidized THC metabolites are not detected by routine screening tests such as immunoassays, and/or confirmatory tests such as analysis by gas chromatography/mass spectrometry (GC/MS). However, such oxidizing agents can be easily detected using standard reagents that react in colorimetric assays to detect peroxidase enzyme activity. These reagents, which are dyes, can either be used in solution or applied to a solid surface to detect the presence of oxidizing adulterants in human urine, such as adulterants added to evade detection of marijuana use.

Generally, a variety of urine adulterants are sold by entities which seek to aid drug abusers in evading detection by urine drug tests. Such adulterants are sold under trade names such as "Whizzies"®, "Klear"® and "Urine Luck"®, but the nature of the adulterant is not generally disclosed. A number of new adulterants have also been introduced via the Internet; the advent of each new adulterant provides a window of time during which users of the adulterant are not detected due to the lack of test methods. Moreover, the increasing number of adulterants has made detection of adulterated samples difficult and costly because of the need for a number of specific tests required to detect adulteration.

The most recent adulterants introduced have been those which prevent detection of the drug of abuse or its metabolite by chemical modification of the drug. These adulterants include sodium or potassium nitrite (Klear®) and pyridinium chlorochromate (Urine Luck®, whose active ingredient is hexavalent chromium (CrVI)). In each case, the new adulterant was designed to evade existing adulteration test methods, the nature of the adulterant was not divulged by the vendor, and identification of the adulterant required significant effort on the part of drug testing laboratories and/or manufacturers of tests to detect drugs of abuse.

Tests have been developed to detect nitrite as an adulterant. These tests are based on the well-known Griess reaction with sulfanilamide and napthylethylenediamine. Tests have also been developed to detect chromium (VI) as an adulterant, based on the reaction of chromium (VI) with 1,5-diphenylcarbazide. These tests have been developed commercially and are sold as Nitrite-Detects and Chromate-Detects assays, respectively (Microgenics Corp., Fremont, Calif.). Each of these tests is specific for the target analyte; for example, the Griess reaction does not detect chromium (VI), whereas 1,5-diphenylcarbazide does not react with nitrite. Samples which test positive by these screening methods are then confirmed for the presence of the drug and/or its metabolite by more specific assays such as ion chromatography, atomic absorption spectroscopy (AAS) or high performance liquid chromatography (HPLC).

Most recently, a new urine adulterant has become available which also acts to chemically modify $\Delta^9 THC$ such that it is not detected by immunoassays and/or other confirmatory methods. This adulterant, termed "Stealth®," is available via the Internet but its chemical identity is currently not widely known. In the inventive method, however, it was discovered that it contained two active components: the enzyme horseradish peroxidase, and the oxidant hydrogen peroxide ($H_2O_2$) Along with this discovery came the unexpected finding that chromogenic substrates for horseradish peroxidase (and other peroxidases) could also be used to detect other adulterants which act to chemically modify THC metabolites.

Stealth® (Cannabis Connections, Lakewood, Ohio) is advertised as a product which prevents detection of drugs of abuse. Stealth® is provided as two components: a tan-colored powder, labeled as "Catalyst," and a colorless liquid, labeled as "Activator." The directions provided with the product indicate that the user should add the Catalyst powder to an empty sample cup, add 60 mL of urine, and then add the Activator liquid and mix.

To confirm the role of horseradish peroxidase and hydrogen peroxide as active ingredients in Stealth®, the following experiment was performed. A fresh urine sample was divided into two aliquots. THC-COOH was added to one of the aliquots to a final concentration of 100 ng/mL and further divided into two additional aliquots. Purified horseradish peroxidase (Sigma Chemical Co., St. Louis, Mo.) was added to one of the aliquots containing THC-COOH to a final concentration of 100 $\mu$g/mL. This concentration was estimated to be equivalent to the peroxidase concentration resulting from addition of the "Catalyst" component to urine, according to the directions for use and based upon estimation of peroxidase content by the results of sodium dodecyl sulfate-polyacrylamide gel electrophoresis (SDS-PAGE) and enzyme activity assays. Hydrogen peroxide (22.5 $\mu$l of 3% $H_2O_2$) was then added to the sample containing the hydrogen peroxidase. This concentration was estimated to be equivalent to the peroxide derived from the "Activator" component, based upon the ultraviolet absorbance of the "Activator" component in comparison with a 3% solution of peroxide. All samples were incubated for 30 min at room temperature and then tested for THC using a commercially available THC immunoassay kit (Microgenics Corp., Fremont, Calif.). A positive result for THC was obtained for the control sample containing only THC-COOH. Negative results were obtained for both the urine aliquot without THC-COOH and for the aliquot containing THC-COOH that had been treated with purified horseradish peroxidase and hydrogen peroxide.

The discovery that Stealth® contained horseradish peroxidase and hydrogen peroxide as active ingredients in the "Catalyst" and "Activator" components, respectively, led to efforts to develop an automated screening test for the presence of Stealth® in urine. To achieve this goal, the peroxidase substrate 3,3'5,5'-tetramethylbenzidine (TMB, Sigma Chemical Co., St. Louis, Mo.) was evaluated. When 5 $\mu$l of horseradish peroxidase (HRP) at 1 $\mu$g/mL was mixed with 125 $\mu$l of hydrogen peroxide (3%) and 125 $\mu$l of TMB (0.1 mg/mL to 0.01 mg/mL), the mixture turned to a light blue color which was monitored at a wavelength of 650 nm. The results of this experiment indicated that this method was very sensitive in detecting the active components of the adulterant, "Stealth".

A surprising result was obtained when the TMB assay was used to test for specificity with other adulterants. Addition of 1–10 mM potassium nitrite to an equal volume of TMB Reagent produced a blue-brown color. Typical concentrations of potassium nitrite, which is the active ingredient in the adulterant "Klear"®, used to prevent detection of marijuana use, are less than 20 mM. Similarly, 10 mM pyridinium chlorochromate, the active component in "Urine Luck"®, added to an equal volume of the TMB reagent produced a strong brown color with precipitate. Pyridinium chlorochromate is typically used at concentrations of greater than 10 mM to block detection of marijuana use.

These surprising and unexpected results provided the basis for the inventive method of detecting adulterants added to urine for the purpose of preventing detection of marijuana use. In general, it appeared that a strong oxidant was necessary to convert THC metabolites, such as THC-COOH, to compounds which are not detected by general or specific methods, such as immunoassays or GC/MS methods. These oxidizing agents include potassium or sodium nitrite, chromium (VI) in the form of pyridinium chlorochromate or potassium dichromate, or horseradish peroxidase and hydrogen peroxide. Such strong oxidizing agents are able to oxidize chromogenic substrates designed for detection of horseradish peroxidase, such as TMB. Weaker oxidizing agents, such as hydrogen peroxide alone, are not able to oxidize THC metabolites or the chromogenic peroxidase substrate, TMB. Thus, as new urine adulteration agents are developed which act via the same mechanism but have new compositions designed to avoid detection by more specific tests, it is likely that they can be detected using chromogenic peroxidase substrates.

The inventive method also includes the use of certain peroxidase substrates in rapid-test or kit methods for detection of urine adulterants which oxidize THC metabolites. Some substrates are slightly soluble in an aqueous environment, and react with peroxidase to form a highly insoluble, colored precipitate. Besides TMB such substrates include diaminobenzidine without or with nickel enhancement, 3-amino-9-ethylcarbazone, 4-chloro-1-napthol, 2,2-azino-bis(3-ethylbenzthiazoline-6-sulfonic acid) (ABTS), o-phenylenediamine (OPD), etc. (Harlow, E. and Lane, D., Antibodies: A Laboratory Manual. Cold Spring Harbor, N.Y.: Cold Spring Harbor Laboratory, 1988, pp. 680–681). In one embodiment TMB alone can be used to detect nitrite and chromium (VI). TMB may be impregnated in a pad to provide a test strip immunoassay. A porous pad impregnated with these substrates, to which an adulterated urine sample was added, produced a color and the product remained in the pad. Use of these peroxidase substrates is well known in immunohistochemistry, Western blots, and a variety of solid-phase immunoassay methods. A rapid-test method for detection of urine adulteration would be valuable as a deterrent of urine adulteration due to the rapid detection at the point of collection. However, the method may also be used in assays routinely performed on clinical analyzer instruments which measure color formation of chromagens in clinical laboratories.

EXAMPLE 1

The chromogenic substrate TMB was reacted with sample solutions of each of the oxidizers $NaNO_2$, chromium VI, peroxidase alone, and peroxidase/hydrogen peroxide combined, to determine the ability of these compounds to oxidize TMB as indicated by the development of a blue color. A buffer containing 10 mM citrate and 1.3 mM EDTA, pH 3.5, was prepared using standard laboratory procedures. The TMB reagent solution was prepared by dissolving 0.047 g TMB (Sigma Chemical Co., St. Louis, Mo.) in 10 g of glycerol and 90 mL of the citrate buffer.

The $NaNO_2$ solution (100 mM) was prepared by dissolving 69 mg $NaNO_2$ (Sigma Chemical Co., St. Louis, Mo.) in 10 mL water. The 100 mM $NaNO_2$ solution was serially diluted with water to prepare $NaNO_2$ solutions with concentrations of 50 mM, 25 mM, 12.5 mM, 6.3 mM, 3.2 mM, 1.6 mM and 0.8 mM.

The chromium VI solution (100 mM) was prepared by dissolving 215.6 mg pyridium chloromate (Sigma Chemical Co., St. Louis, Mo.) in 10 mL water. The 100 mM chromate solution was serially diluted with water to prepare solutions with concentrations of 50 mM, 25 mM, 12.5 mM, 6.3 mM, 3.2 mM, 1.6 mM, and 0.8 mM.

The hydrogen peroxide solution ($1\%^{v/v}$) was prepared from a 30% hydrogen peroxide solution using standard laboratory procedures. A peroxidase solution with a concentration of 100 ug/mL was prepared by dissolving 1.0 mg of horseradish peroxidase (Sigma Chemical Co., St. Louis, Mo.) in 10 mL phosphate buffered saline (PBS, pH 7.4), containing $1\%^{w/v}$ bovine serum albumin (BSA). This peroxidase solution was serially diluted with the PBS/BSA solution to prepare solutions with concentrations of 50 $\mu$g, 25 $\mu$g, 12.5 $\mu$g, 6.3 $\mu$g, 3.2 $\mu$g, 1.6 $\mu$g, and 0.8 $\mu$g peroxidase/mL. Other types of peroxidases may also be used such as that from soybean and *Arthromyces ramosus*.

One mL of the TMB reagent was mixed with 0.1 mL of each of the $NaNO_2$, chromate and peroxidase solutions and with 0.1 mL aliquots of the peroxidase solutions, and the combined peroxidase/$H_2O_2$ solution (0.1 mL and 0.01 mL, respectively).

The results are shown in the following table.

TABLE 1

Color Intensities for TMB Reactions with Oxidizer and Peroxidase Solutions

| | 100 | 50 | 25 | 12.5 | 6.3 | 3.2 | 1.6 | 0.8 | 0 |
|---|---|---|---|---|---|---|---|---|---|
| Concentrations of Oxidizers mM | | | | | | | | | |
| $NaNO_2$ | +8 | +7 | +6 | +5 | +4 | +3 | +2 | +1 | 0 |
| Chromate | +7 | +7 | +7 | +5 | +4 | +3 | +2 | +1 | 0 |
| Concentrations of Peroxidase $\mu$g/mL | | | | | | | | | |
| Peroxidase | 0 | 0 | 0 | 0 | 0 | 0 | 0 | 0 | 0 |
| Peroxidase with $H_2O_2$ | +8 | +8 | +8 | +8 | +6 | +4 | +3 | +1 | 0 |

With TMB and peroxidase alone, there was no color change at any concentration.

With TMB and $NaNO_2$, and TMB and chromate the color changed to blue. On a scale of one to ten, with ten being the most intense color, the color intensity ranged from eight with the 100 mM of $NaNO_2$ and seven with 100 mM of chromate, to one with 0.8 mM of either $NaNO_2$ or chromate.

With TMB and the combined peroxidase/$H_2O_2$ solution, the color changed to blue with an intensity ranging from eight with 100 $\mu$g peroxidase/mL, to one for 0.8 $\mu$g peroxidase/mL.

EXAMPLE 2

A chromogenic substrate, ABTS, was reacted with sample solutions of each of the oxidizers $NaNO_2$, chromium VI, peroxidase alone, and peroxidase/hydrogen peroxide combination to determine the ability of these compounds to oxidize TMB as indicated by the development of a blue color. The ABTS reagent solution was prepared by dissolving 10 mg ABTS (Sigma Chemical Co., St. Louis, Mo.) in 100 mL phosphate buffer, pH 7.4.

The oxidizer and peroxidase solutions at various concentrations, hydrogen peroxide, buffers, and the formation of the reaction mixtures were prepared as described in Example 1. The results are shown in the following table.

TABLE 2

Color Intensities for ABTS Reactions with Oxidizer and Peroxidase Solutions

| | 100 | 50 | 25 | 12.5 | 6.3 | 3.2 | 1.6 | 0.8 | 0 |
|---|---|---|---|---|---|---|---|---|---|
| Concentrations of Oxidizers mM | | | | | | | | | |
| $NaNO_2$ | +8 | +7 | +6 | +3 | +2 | +1 | +1 | +1 | 0 |
| Chromate | +8 | +8 | +7 | +7 | +7 | +6 | +3 | +2 | 0 |
| Concentrations of Peroxidase $\mu$g/mL | | | | | | | | | |
| Peroxidase | 0 | 0 | 0 | 0 | 0 | 0 | 0 | 0 | 0 |
| Peroxidase with $H_2O_2$ | +8 | +8 | +8 | +8 | +7 | +4 | +3 | +1 | 0 |

With ABTS and peroxidase alone, there was no color change at any concentration.

With ABTS and $NaNO_2$, and ABTS and chromate the color changed to blue. On a scale of one to ten, with ten being the most intense, the color intensity ranged from eight with 100 mM of either $NaNO_2$ or chromate, to one with 0.8 mM of $NaNO_2$ and to two with 0.8 mM chromate.

With ABTS and the combined peroxidase/$H_2O_2$ solution, the color changed to blue with an intensity ranging from eight with 100 $\mu$g peroxidase/mL, to three with 0.8 $\mu$g peroxidase/mL.

EXAMPLE 3

A chromogenic substrate, OPD, was reacted with sample solutions of each of the oxidizers $NaNO_2$, chromium VI, peroxidase alone, and peroxidase/hydrogen peroxide combination to determine the ability of these compounds to oxidize OPD as indicated by the development of a blue color. The oxidizer and peroxidase solutions at various concentrations, hydrogen peroxide, buffers, and the formation of the reaction mixtures were prepared as described in Example 1. The OPD reagent was prepared by dissolving 0.05 g OPD in 100 mL of citrate buffer. The results are shown in the following table.

TABLE 3

Color Intensities for OPD Reactions with Oxidizer and Peroxidase Solutions

|  | 100 | 50 | 25 | 12.5 | 6.3 | 3.2 | 1.6 | 0.8 | 0 |
|---|---|---|---|---|---|---|---|---|---|
| Concentrations of Oxidizers mM | | | | | | | | | |
| $NaNO_2$ | +8 | +7 | +7 | +6 | +5 | +1 | +1 | +0 | 0 |
| Chromate | +8 | +7 | +7 | +6 | +6 | +4 | +3 | +1 | 0 |
| Concentrations of Peroxidase µg/mL | | | | | | | | | |
| Peroxidase | 0 | 0 | 0 | 0 | 0 | 0 | 0 | 0 | 0 |
| Peroxidase with $H_2O_2$ | +8 | +8 | +8 | +7 | +7 | +6 | +3 | +1 | 0 |

With OPD and peroxidase alone, there was no color change at any concentration.

With OPD and $NaNO_2$, and TMB and chromate, the color changed to blue. On a scale of one to ten, with ten being the most intense color, the color intensity ranged from eight with 100 mM of either $NaNO_2$ or chromate, to one with 1.6 mM concentration of $NaNO_2$, and to one with 0.8 mM chromate.

With OPD and the combined peroxidase/$H_2O_2$ solution the color changed to blue with an intensity ranging from eight with 100 µg peroxidase/mL, to one with 0.8 µg peroxidase/mL.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

What is claimed is:

1. A method for detecting an oxidant chemical added to adulterate a biological sample comprising reacting said sample with a chromogenic substrate for a peroxidase and thereafter monitoring said sample for production of said chromogen indicating the presence of said oxidant chemical.

2. The method of claim 1 wherein said sample is submitted for drug testing.

3. The method of claim 2 wherein said sample is urine.

4. The method of claim 1 wherein said oxidant chemical is selected from the group consisting of nitrite, chromium VI, and peroxidase/hydrogen peroxide.

5. The method of claim 4 wherein said nitrite is selected from the group consisting of potassium nitrite and sodium nitrite.

6. The method of claim 4 wherein said chromium VI is pyridinium chlorochromate.

7. The method of claim 1 wherein said oxidant chemical oxidizes 11-nor-delta-9-tetrahydrocannabinol-9-carboxylic acid ($\Delta^9$ THC) to render said metabolite undetectable by a screening or confirmatory assay for $\Delta^9$ THC.

8. The method of claim 1 wherein said monitoring is done using a clinical analyzer.

9. The method of claim 8 wherein said clinical analyzer measures color formation of the chromagen.

10. The method of claim 1 wherein said sample is monitored on a test strip containing said chromogenic substrate.

11. The method of claim 1 wherein said sample is monitored by visual inspection.

12. The method of claim 1 wherein said substrate is selected from the group consisting of 3,3',5,5'-tetramethylbenzidine, diaminobenzidine, 3-amino-9-ethylcarbazone, 4-chloro-1-napthol, 2,2-azino-bis(3-ethylbenzthiazoline-6-sulfonic acid, and ortho-phenylenediamine.

13. A device to detect adulteration of a biological sample provided by an individual with a chemical oxidant that prevents detection of marijuana use by said individual comprising a sample-contacting pad containing a substrate that forms a chromogen in the presence of said oxidant.

14. The device of claim 13 wherein said pad is affixed to a backing to form a test strip.

15. The device of claim 13 further comprising a sample application site.

16. The device of claim 13 wherein said substrate is selected from the group consisting of 3,3',5,5'-tetramethylbenzidine, diaminobenzidine, 3-amino-9-ethylcarbazone, 4-chloro-1-napthol, 2,2-azino-bis(3-ethylbenzthiazoline-6-sulfonic acid, and ortho-phenylenediamine.

17. A method to detect adulteration of a urine sample with an oxidant chemical to prevent a positive drug test of said sample comprising adding a chromogenic peroxidase substrate to said adulterated sample and monitoring said sample for an increased absorbance indicating formation of said chromogen in the presence of said oxidant.

* * * * *

UNITED STATES PATENT AND TRADEMARK OFFICE
CERTIFICATE OF CORRECTION

PATENT NO. : 6,503,726 B2
DATED : January 7, 2003
INVENTOR(S) : Anne et al.

It is certified that error appears in the above-identified patent and that said Letters Patent is hereby corrected as shown below:

Column 1,
Line 34, reads "non detectable" and should read -- nondetectable --.

Column 2,
Line 11, reads "acid, and" and should read -- acid), and --.

Column 3,
Line 7, reads "Nitrite-Detects and Chromate-Detects" and should read -- Nitrite-Detect® and Chromate-Detect® --.
Line 24, reads "(H202) Along" and should read -- (H202). Along --.

Column 4,
Line 4, reads "3,3'5,5' - tetramethyl" and should read -- 3,3', 5, 5' - tetramethyl --.
Line 12, reads "adulterant, "Stealth"." and should read -- adulterant, Stealth®. --

Column 5,
Line 34, reads "ug/mL" and should read -- µg/mL --.

Column 8,
Line 23, reads "acid, and" and should read -- acid), and --.
Line 38, reads ""acid, and" and should read -- acid), and --.

Signed and Sealed this

Fifteenth Day of July, 2003

JAMES E. ROGAN
*Director of the United States Patent and Trademark Office*